United States Patent
Frank

(10) Patent No.: US 8,882,799 B2
(45) Date of Patent: Nov. 11, 2014

(54) MEDICAL INSTRUMENT FOR GRASPING AN OBJECT, IN PARTICULAR A NEEDLE HOLDER

(75) Inventor: Timothy Graham Frank, Scotland (GB)

(73) Assignee: University of Dundee (GB)

( * ) Notice: Subject to any disclaimer, the term of this patent is extended or adjusted under 35 U.S.C. 154(b) by 0 days.

(21) Appl. No.: 13/469,441

(22) Filed: May 11, 2012

(65) Prior Publication Data

US 2012/0289999 A1 Nov. 15, 2012

(30) Foreign Application Priority Data

May 11, 2011 (EP) ..................................... 11165696

(51) Int. Cl.
| | | |
|---|---|---|
| A61B 17/28 | (2006.01) | |
| A61B 17/062 | (2006.01) | |
| A61B 17/29 | (2006.01) | |
| A61B 17/00 | (2006.01) | |

(52) U.S. Cl.
CPC ....... *A61B 17/062* (2013.01); *A61B 2017/2936* (2013.01); *A61B 2017/00407* (2013.01); *A61B 2017/2934* (2013.01); *A61B 2017/2946* (2013.01)
USPC .......................................... 606/205; 606/174

(58) Field of Classification Search
USPC ........ 606/205, 144, 139, 174, 208; 227/175.1
See application file for complete search history.

(56) References Cited

U.S. PATENT DOCUMENTS

| | | | | |
|---|---|---|---|---|
| 5,392,789 A | * | 2/1995 | Slater et al. .................... | 600/564 |
| 5,409,498 A | * | 4/1995 | Braddock et al. ............. | 606/143 |
| 6,270,508 B1 | * | 8/2001 | Klieman et al. ............... | 606/147 |
| 7,628,791 B2 | * | 12/2009 | Garrison et al. ................ | 606/51 |
| 7,896,900 B2 | * | 3/2011 | Frank et al. ..................... | 606/208 |
| 8,083,765 B2 | * | 12/2011 | Lee et al. ........................ | 606/205 |
| 2001/0016750 A1 | * | 8/2001 | Malecki et al. ............... | 606/158 |

FOREIGN PATENT DOCUMENTS

| | | |
|---|---|---|
| DE | 20001492 U1 | 6/2000 |
| EP | 1872729 A1 | 1/2008 |
| EP | 2392282 A1 | 12/2011 |
| WO | 2004032754 A2 | 4/2004 |
| WO | 2005092216 A1 | 10/2005 |

OTHER PUBLICATIONS

European Search Report Application No. EP 12 16 7507 Completed: Sep. 14, 2012; Mailing Date: Oct. 2, 2012 7 pages.

* cited by examiner

*Primary Examiner* — Thomas McEvoy
*Assistant Examiner* — Julie A Szpira
(74) *Attorney, Agent, or Firm* — St. Onge Steward Johnston & Reens LLC

(57) ABSTRACT

The present invention relates to a medical instrument for grasping an object, in particular a surgical needle holder, with two jaw parts arranged at a distal end of a shaft, at least one of the jaw parts being pivotable with respect to the other one of the jaw parts between a grasp state for grasping the object between the jaw parts and a release state for releasing the object, and with a latching mechanism comprising at least one latching element, wherein the latching element has an elongated opening to accommodate a connection pin for connecting the at least one pivotable jaw part with the latching element, and wherein the elongated opening is divided in several sections along its length by periodical projections, such that the at least one pivotable jaw part pivots stepwise from one stable latched position to another stable latched position.

34 Claims, 6 Drawing Sheets

MEDICAL INSTRUMENT FOR GRASPING AN OBJECT, IN PARTICULAR A NEEDLE HOLDER

CLAIM OF PRIORITY

The present invention claims priority from European Patent Application No. 11 165 696.3, filed May 11, 2011, of common title and inventorship herewith.

FIELD OF THE INVENTION

The present invention relates to a medical instrument for grasping an object, in particular a surgical needle holder.

BACKGROUND OF THE INVENTION

An instrument comprising a latching mechanism is known from EP 1 872 729 A1.

In this instrument, a latching element is realized by an arc-shaped lever, which is attached with one end of the arc at the force transmission element and with the other end of the arc attached to the at least one pivotable jaw part. While the location of a connection between the latching element and the transmission element is distal from the location of a connection of the latching element with the at least one pivotable jaw part in the release state, the location of the connection of the latching element with the transmission element is moved in proximal direction by pulling on the transmission element via the at least one operating element. This leads to a pivot of the at least one pivotable jaw part and results in a closing of the jaw parts. The two aforementioned locations connected via the flexible arc-shaped element, i.e. the latching element, are thereby getting closer together, until an end point is reached wherein the location of the connection between arc-shaped element and transmission element lies slightly proximal with respect to the connection location of the arc-shaped element and the pivotable jaw part. In this position, an over-center state is reached, which is possible because of the flexibility of the latching element, i.e. the arc-shaped element. This stable state forms the basis of the latching mechanism.

As the instrument is equipped to accommodate objects of different diameter, the aforementioned latching mechanism has to be formed in that way that even with a small object, e.g. a needle of small diameter, the arc-shaped element has to be flexed at least a little in order to provide a working latching mechanism.

When accommodating larger objects, such as needles comprising a larger diameter, this results in a much higher flexing of the arc-shaped element and, therefore, in a higher strain for the material. This means that due to the higher and often different stress acting on the latching element, a high amount of strain occurs, which may exceed the elastic limit of the construction material resulting in permanent bending damage.

In order to decrease this strain, the aforementioned citation suggests to equip the part of the at least one pivotable jaw part which connects with the latching element with a certain flexibility. However, even here a permanent strain occurs after some time, due to the flexing movements.

Further, due to the limitations given by the material properties and the design of such a small mechanical instrument and mechanism, the needle holding force and the maximum jaw opening angle are both sub-optimal. This is also due to the aforementioned needed capability of this instrument to accommodate small as well as larger objects.

Further, WO 2005/092216 A1 shows an instrument used for surgical laparoscopy. This instrument is designed such that a pivotable jaw part comprises a pin at the opposite end with respect to the cutting part of the jaws. This pin is slidingly received in a groove of an axially moveable element. The groove may comprise an elevation shift at its bottom. In this elevation shift the aforementioned pin may be temporarily received while the pin moves along this groove due to the axial movement of the element. This results in a temporarily lock of the pin without affecting the linear motion of the jaws relative to the handle actuation.

This design comprises only one locked position as well. Also, due to the design with the short pin being slidingly arranged in a groove the locked position is not very stable, especially when stronger forces are applied in order to hold the aforementioned objects, like needles. Also, for the same reasons a twisting of the jaw parts in the direction of the pivot axis may occur due to the strong forces acting on the jaw parts when the aforementioned objects are grasped.

It is therefore an object of the present invention to improve the medical instruments of the kind mentioned before, such that the aforementioned drawbacks are avoided, in particular that the instrument is capable to accommodate objects of different sizes safely with the necessary holding force between the two jaw parts while simultaneously the strain in the parts is eliminated or at least reduced.

SUMMARY OF THE INVENTION

The object is achieved by a medical instrument for grasping an object, in particular a surgical needle holder, comprising:
- an elongated shaft, having a proximal and a distal end,
- an axially movable force transmission element running within the shaft,
- two jaw parts arranged at the distal end of said shaft, at least one of the jaw parts being pivotable with respect to the other one of the jaw parts,
- a connection element for operatively connecting said force transmission element with the at least one pivotable jaw part,
- a connection pin,
- a handle arranged at the proximal end of the shaft,
- the handle having at least one operating element for moving the at least one pivotable jaw part, and
- a latching mechanism,
- the latching mechanism comprising:
  - at least one latching element being at least a part of the connection element, and
  - at least three latching positions,
- the latching element comprising an elongated opening to accommodate the connection pin,
- the elongated opening comprising:
  - two opposing longer walls, and
  - periodical projections on at least one of the opposing walls along the length of the elongated opening,
- wherein the at least one pivotable jaw part is pivotable between a grasp state for grasping the object between the jaw parts and a release state for releasing the object by the operating element, and the axially movable force transmission element is operatively connected with the at least one operating element and with the at least one pivotable jaw part via the connection element,
- the at least one pivotable jaw part can be immobilized in the grasp state by the latching mechanism, wherein the latching element is operatively connected to the force transmission element and the at least one pivotable jaw part, the at least one pivotable jaw part being connected with the latching element via the connection pin, and wherein the elongated opening is divided in several sections along its length, the sections being formed by the periodical projections, and wherein each of the sections forms one of the latching positions, such that the at least one pivotable jaw part pivots stepwise from one stable latched position to another stable latched position, when the transmission element is moved axially, wherein the latching mechanism preferably comprises three to eight latching positions, and more preferably comprises three to five latching positions In contrast to the aforementioned instruments, the instrument of the present invention does not comprise only one latching position, it comprises at least three, preferably three to eight and more preferably three to five. By such an arrangement, there are several latched positions of the at least one pivotable jaw part, each of them can be regarded as a stable state. Because of the plurality of the stable states resulting from this arrangement, an object, e.g. a surgical needle, can be accommodated and held by the two jaw parts fixedly in at least one of these stable states. Accordingly, for every object that shall be grasped by the medical instrument of the present invention, a secure position for the at least one pivotable jaw part with respect to the other jaw part exists, in which the object can be held safely with the medical instrument of the present invention, independent of the size of the object to be held, provided the size is within a range capable to be held by the medical instrument of the present invention having itself limits based on the given size of the jaw parts.

Providing several stable latched states or latching positions of the jaw parts, rather than having just one latched state for all objects of possible sizes, reduces the strain that occurs to the elements that are part of the latching mechanism.

It has been observed that providing at least three, preferably three to eight and more preferably three to five, latching positions as stable positions of the at least one pivotable jaw part with respect to the other jaw part, is sufficient for the instrument of the present invention comprising a common size, in order to accommodate all common objects that shall be grasped. The range from three to eight, preferably three to five, represents that range in which there are enough possible latching positions. At the same time, the amount of latching positions is delimited, in order to maintain a required stability of the elements involved in the latching mechanism. Increasing the amount of latching positions would inevitably result in the usage of smaller mechanical parts. As these are again more easily targets for strain, such designs are counterproductive.

The division into sections is easily achieved by even just a small projection on at least one of the opposing longer walls of the elongated opening. Since such an arrangement is easy to be manufactured, the effort and cost for providing an instrument of the present invention is minimized with respect to this feature. In order to achieve the grasp state, the connection pin just needs to move past the projections until it reaches the section that corresponds to the desired grasp state. Once the desired grasp state has been reached the connection pin rests against the previous projection in such a way as to maintain the grasp state. At the same time, a movement of the connection pin to the next section, i.e. by moving past the next projection, is blocked as the at least one pivotable jaw part is unable to pivot further due to the object between the jaw parts.

Instead of describing the division into several sections by periodical projections within the elongated opening as mentioned before, this constructive design may be also described by wells or dents being comprised within the elongated opening. This means that one can also regard this separation into several sections being realized by at least one of the opposing walls comprising several wells or dents along the length of the elongated opening.

In an embodiment of the present invention, one of the latching position forms the grasp state.

The advantage from this is that in the grasp state the jaw parts are arranged in a secured manner with respect to each other, resulting in a safe and strong grasped object. It is further beneficial that any of the latched positions mentioned before is able to form the grasp state. Thereby, the possibility for grasping objects of different sizes in a safe and strong hold is achieved.

In another embodiment of the present invention, the latched position forming the grasp state and a latched position forming the release state are achieved by the furthermost movement of the force transmission element in one respective axial direction when interacting with the object to grasp.

This measure has the advantage that both necessary states, i.e. the grasp state and the release state, are achieved just by moving the force transmission element in one respective axial direction, i.e. in proximal or distal direction. This is preferably done by using the operating element. Accordingly, a user just needs to push or pull the operating element to one respective end, in order to achieve a grasp state or the release state. This is an easy way of operating the medical instrument of the present invention, as the latched positions responsible for grasping the object are reached automatically.

In another embodiment of the present invention, the force transmission element comprises a distal end, and the connection element is arranged at the distal end of said force transmission element in that way that it undergoes the same axial movements as the force transmission element.

This arrangement has the advantage that it is very easy to attach the connection element to the force transmission element. This can, for example, simply be done by measures known in the art, e.g. gluing, welding, screwing, or any other fit mechanisms, like latching mechanisms. This contributes to a simple design of the instrument of the present invention, while simultaneously achieving a versatile instrument in which this connection element can be replaced or exchanged, if necessary.

In another embodiment of the present invention, the elongated opening is arranged in that way, that a movement of the latching element by an axial movement of the force transmission element results in a pivot of the at least one pivotable jaw part by movement of the connection pin within the elongated opening.

This design has the advantage that thereby a transfer of the axial movement of the transmission element and the latching element, which is connected thereto via the connection element, into a rotational movement for the at least one pivotable jaw part, is easily achieved. By such an arrangement, the connection pin for connecting the at least one pivotable jaw part with the latching element is basically just movable within the elongated opening and, accordingly, no flexible parts are needed for this latching mechanism in order to transfer the axial movement into a rotational movement. In contrast to this, the device mentioned at the outset used for this, is the flexible, arc-shaped lever. Here, only strain can occur on the connection pin that moves within the elongated opening along the given way based on the constraints resulting from the walls of the elongated opening.

In another embodiment of the present invention, the elongated opening is arc-shaped.

The advantage of this design of the elongated opening contributes to a more easily transfer of the axial movement into a rotational movement. The strain of the connection element and, accordingly, latching element, by strains resulting from this transfer, is thereby eliminated.

In another embodiment of the present invention, the latching element comprises two opposing faces and the elongated opening passes through the latching element from one of the faces to the other one of the faces, wherein the connection pin preferably passes substantially through the elongated opening.

Within the context of the present invention the expression "passes substantially through" is to be understood in such a way that the pin may pass through and protrude from the opening on both sides, as well as that one end of the pin may also be flush with the face of the latching element or even that said end of the pin may also lie within the elongated opening, provided that a contact area between the connection pin and the surface within the elongated opening is such that an adequate force transmission to the at least one pivotable jaw part is possible for grasping the object.

The connection pin passing through the elongated opening of the latching element results in a stable arrangement and reliable transmission of force from the force transmission element to the at least one pivotable jaw part. It is thereby particularly preferred if the at least one pivotable jaw part is connected to the two opposing ends of the pin. While the connection pin can be connected to the at least one moveable jaw part at any point along the length of the jaw part, it is preferred if the connection between the pin and the jaw part is arranged at or near the proximal end of the at least one moveable jaw part, as such an arrangement will result in an even distribution of the force transmitted from the force transmission element to the jaws. As a consequence, a twisting of the jaw parts does not occur while grasping an object.

In another embodiment of the present invention, the connection pin can move from one of the sections to another one of the sections being latched in each.

This way, the latching mechanism according to the present invention is achieved in a simple but effective constructive way. Therefore, the connection pin is the main component that operatively connects the at least one pivotable jaw part to the aforementioned latching element. Keeping the parts of a mechanism at a minimum like this has the further advantage of the whole device being easy to be cleaned.

In another embodiment of the present invention, the connection pin comprises a surface having a reduced coefficient of friction.

The term "reduced coefficient of friction" refers to the latching element and the elongated opening with its opposing longer walls and shall be understood in comparison to the case wherein the material of the longer walls and the surface of the connection pin are both made of steel. Referring to the surface of the connection pin includes the cases wherein the whole connection pin is manufactured from this material as well as that the connection pin comprises a coating of such a material.

Although, the connection pin shall be latched in the aforementioned latching positions, the movement from one latching position to another latching position, that is to say from one section to another section shall preferably be possible without the interference of friction while the connection pin moves within the elongated opening over at least one of the aforementioned opposing longer walls of the latter. This is achieved by the surface of the connection pin having a reduced friction. This low friction surface may be present over the whole connection pin, a part of the connection pin that may be exposed to the outside or at least on that area of the connection pin that gets in contact with the opposing longer walls of the elongated opening.

In another embodiment of the present invention, the connection pin comprises a surface of Polytetrafluoroethylene.

Such a surface of Polytetrafluoroethylene (e.g. Teflon®) has the advantage that when applied at least to the areas that get in contact with the inside of the elongated opening, the friction may be significantly reduced. Further, Polytetrafluoroethylene is resistant to the harsh conditions used in disinfection of a medical compound, like high temperatures in autoclaves and chemicals. Also, Polytetrafluoroethylene provides a surface that is easy to clean and disinfect. As mentioned before, the surface may be the result of at least partially coating the connection pin or of the connection pin being manufactured from Polytetrafluoroethylene. Also, the reduced friction according to the present invention may also result if both, the surface of the connection pin and the surfaces within the elongated opening are covered with and/or manufactured from Polytetrafluoroethylene.

In another embodiment of the present invention, the connection pin comprises a roller, the roller being arranged between the opposing walls and being moveable along the length of the elongated opening.

The usage of a roller has the advantage that the aforementioned strain of the connection pin is reduced, due to a certain flexibility of the roller. Further, the roller also shows the desired lower frictional characteristics. This reduction in friction has again the advantage that the movement of the roller within the elongated opening is more easy.

In a preferred embodiment of the present invention, each of the sections accommodates the roller via form-fit, and the roller is able to move from one of the sections to another one of the sections.

This measure has the advantage that the roller cannot accidentally slide along the elongated opening, thereby leading to an unwanted movement of the at least one pivotable jaw part in either direction. On the other hand, given a suitable design, easy movement of the roller from one section to another section is still possible. For this purpose, the user just has to overcome the barrier given by the form-fit of the roller within the respective section. Thereby a latching mechanism comprising several latching positions is easily achieved.

In another embodiment of the present invention, the connection element comprises at least one sliding roller, and the connection element is arranged in the shaft and gets in contact with the shaft via the sliding roller.

This measure has the advantage that the connection element itself cannot get directly in contact with the inner wall of the shaft. This results in a highly reduced friction and, accordingly, in an easily movable connection element. The sliding roller itself shows low friction, as it rolls over the inside wall of the shaft. For this, the roller is preferably arranged on the connection element via a pin.

In another embodiment of the present invention, the at least one pivotable jaw part comprises a proximal portion being elastically deformable.

This measure has the advantage that some strains that may even occur with the device of the present invention can be compensated by this elastically deformable proximal portion. This means that even by the application of a stronger force on the force transmission element, e.g. by a user or an operator, the forces acting on the elements taking part in the latching mechanism are reduced because of this flexibility.

This contributes in a positive way to the minimization of damage in the latching mechanism, even in the case of an accidentally improper use of the instrument of the present invention.

The aforementioned object is further achieved according to another aspect of the present invention by a medical instrument for grasping an object, in particular a surgical needle holder, comprising:
- an elongated shaft, having a proximal and a distal end,
- an axially movable force transmission element running within the shaft,
- two jaw parts arranged at the distal end of the shaft, at least one of the jaw parts being pivotable with respect to the other one of the jaw parts,
- a connection element for operatively connecting the force transmission element with the at least one pivotable jaw part,
- a connection pin,
- a handle arranged at the proximal end of the shaft,
- the handle having at least one operating element for moving the at least one pivotable jaw part,
- a latching mechanism,
- the latching mechanism comprising:
  - at least one latching element being at least a part of the connection element, and
  - at least three latching positions,
- the latching element comprising:
  - two opposing faces, and
  - an elongated opening to accommodate the connection pin, comprising two opposing longer walls, the elongated opening passing through the latching element from one of the faces to the other one of the faces,
- wherein the at least one pivotable jaw part is pivotable between a grasp state for grasping the object between the jaw parts and a release state for releasing the object, and the axially movable force transmission element is operatively connected with the at least one operating element and with the at least one pivotable jaw part via the connection element,
- the at least one pivotable jaw part can be immobilized in the grasp state by the latching mechanism,
- wherein the latching element is operatively connected to the transmission element and the at least one pivotable jaw part,
- the at least one pivotable jaw part being connected with the latching element via the connection pin, and
- wherein the connection pin passes substantially through the elongated opening, and the elongated opening is divided in several sections along its length, and wherein each of the sections forms one of the latching positions, such that the at least one pivotable jaw part pivots stepwise from one stable latched position to another stable latched position, when the transmission element is moved axially.

In an embodiment of this aspect of the present invention the elongated opening comprises periodical projections on at least one of the opposing walls along the length of the elongated opening.

Further embodiments according to this aspect of the present invention and the according advantages can be obtained by combining this aspect of the present invention with one or several of the features mentioned above in connection with the embodiments of the first aspect. Any such combination is considered part of the scope and disclosure of the present invention.

Further features and advantages will become apparent from the following description and the accompanying drawings.

It is to be understood that the features mentioned before and those features still to be explained below are not only applicable in the combinations given, but also in other combinations or in isolation, without departing from the scope of the invention.

BRIEF DESCRIPTION OF THE DRAWINGS

The invention is described and explained in more detail below with reference to a few exemplary embodiments of the invention in association with the accompanying drawings, in which.

DETAILED DESCRIPTION OF PREFERRED EMBODIMENTS

Figure 1:
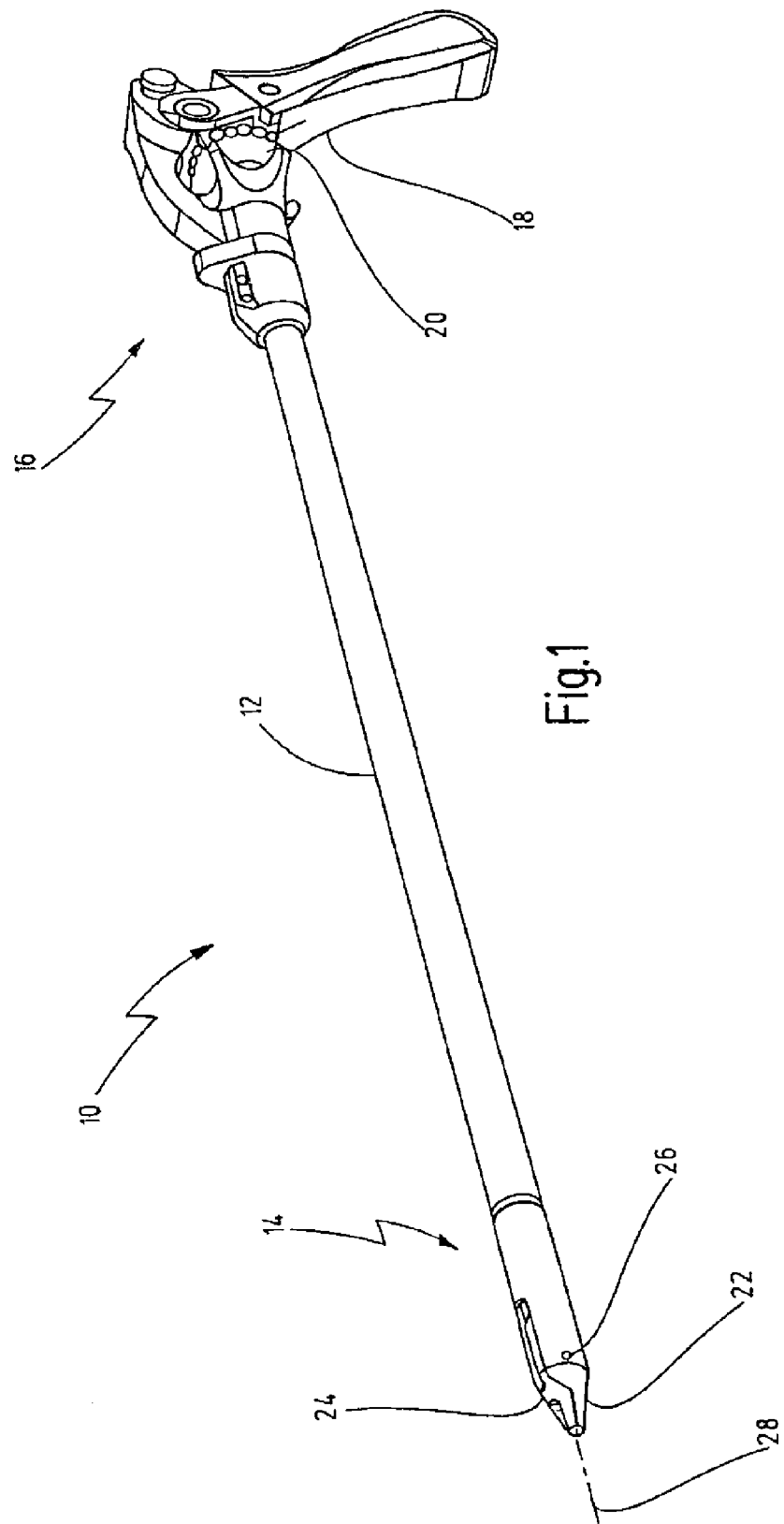
FIG. 1 shows an embodiment of the instrument of the present invention in a perspective total view.

An embodiment of a medical instrument according to the present invention is described hereinafter and is shown throughout FIGS. 1 to 6 in its entirety by the reference numeral 10. Further embodiments of a medical instrument according to the present invention are also described with reference to FIGS. 7 to 10 and shown hereinafter by the reference numerals 100 and 150.

The medical instrument 10 comprises a shaft 12 having a distal part 14 and a proximal part 16.

At the proximal part 16, there is arranged a handle 18 which itself comprises an operating element 20 which will be described later in more detail.

At the distal part 14, the medical instrument 10 comprises two jaw parts 22 and 24. In this embodiment, one of those jaw parts is a fixed jaw 22, wherein the other jaw part is a pivotable jaw 24. The pivotable jaw part 24 pivots around a pivot axis 26. Within the shown embodiment, the pivot axis 26 runs transversely through a central longitudinal axis 28 of the shaft 12.

Coming now to the representation in FIG. 2, the interior of the medical instrument in the distal part 14 can be seen and will be described hereinafter.

In order to simplify the shown drawings, the shaft 12 is here just shown with its very distal part.

Within shaft 12 runs a force transmission element 30. This force transmission element 30 comprises a helical section 32, which is beneficial for the transmission of turning forces along the force transmission element 30 as it is described within EP 1 872 729 A1, as mentioned at the outset.

The force transmission element 30, here only shown in its distal end area, is at its proximal end connected to the aforementioned operating element 20.

By an operation of the operating element 20, e.g. a push or pull movement, the force transmission element 30 is moved axially along the central longitudinal axis 28 in distal or proximal direction, as it is implied by a double arrow 34. Apart from this mode of operation, other mechanisms are possible with respect to the operating element 20, e.g. that a rotation of the operating element 20 leads to an axial movement of the force transmission element 30.

At its distal end, the force transmission element 30 is connected to a connection element 36. The connection element 36 comprises in its distal end area a latching element 38, which will be described in more detail hereinafter, and a sliding roller 40. When reference is made to the distal end of the connection element 36 within the context of the present representations such reference may also be regarded as a reference to the latching element 38 in these embodiments and may be understood as such and vice-versa.

The sliding roller 40 is arranged rotatably via a roller pin 42 on the connection element 36. As it projects from the connection element 36, the roller 40 prevents the contact of the connection element 36 with the inside wall of the shaft 12. Thereby, a frictional contact of the connection element 36 with the inner wall of the shaft 12 is avoided. Furthermore, the rotational arrangement of the roller 40 via a roller pin 42 avoids even a frictional interaction of the sliding roller 40 with the wall itself, so that the distal end of the force transmission element 30, i.e. the connection element 36, is able to easily slide back and forth with the directly connected force transmission element 30 as described before and as implied by double arrow 34.

In the embodiment described here, the sliding roller 40 is held via the roller pin 42 between two outer faces or sidewalls 44 and 44' of the connection element 36. This can be seen in more detail in the exploded view of FIG. 3.

Figure 3:
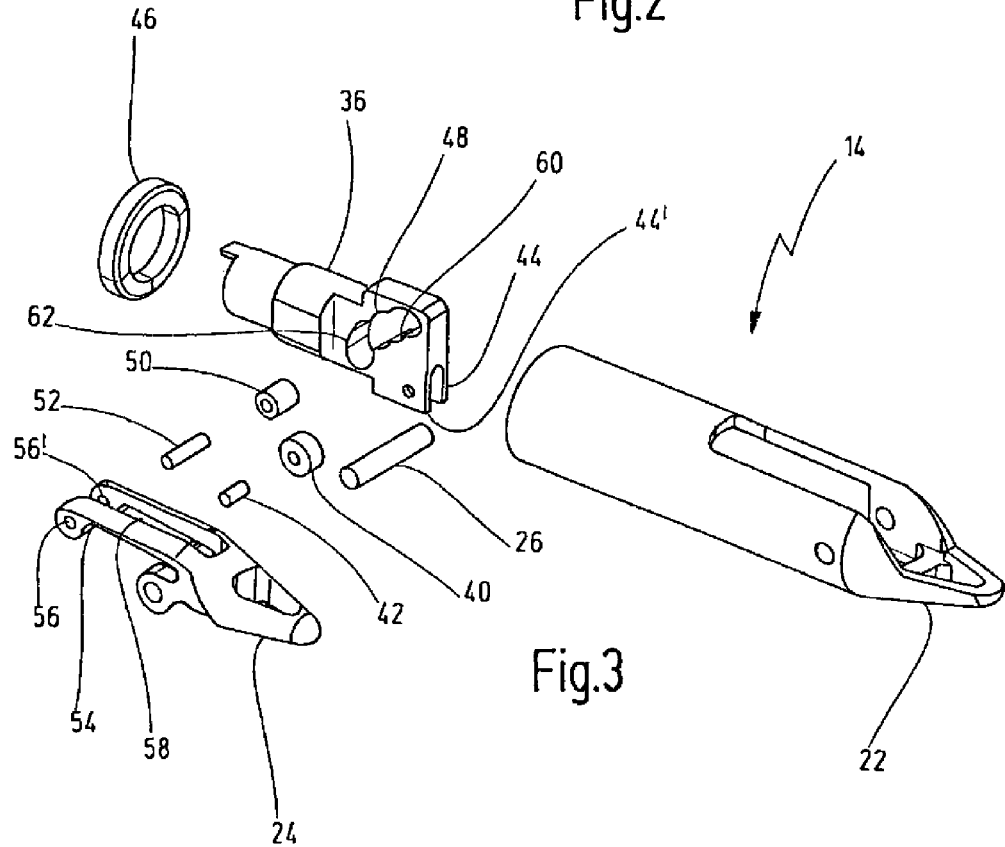
FIG. 3 shows an exploded view of the distal portion shown in FIG. 2, FIGS. 4a-4d show schematic representations of a distal portion of an instrument according to the present invention similar to FIG. 2, each in another latched position of the at least one pivotable jaw part.

As shown in FIG. 3 as well, the distal part 14 of the shaft 12 is connected via a connection ring 46 to the remaining part of shaft 12. Such an arrangement has the advantage that the distal part 14 might be movable with respect to the remaining part of shaft 12 around the central longitudinal axis 28. For this, the embodiment comprising a helical section 32 of the force transmission element 30 is advantageous, as described earlier.

The connection element 36 further comprises an elongated opening 48. This elongated opening 48 is basically arc-shaped in the present embodiment. It passes through the connection element 36 or latching element 38 from one face 44 to the other, i.e. the opposite face 44', as can been seen in FIG. 3. In this special embodiment, a roller 50 is accommodated in this elongated opening 48. The roller 50 itself is arranged via a connection pin 52 at a proximal end 54 of the at least one pivotable jaw 24. For this, the proximal end 54 comprises two openings 56 and 56' for receiving the connection pin 52. This way, the connection pin 52 is connected to the at least one pivotable jaw part 24 with its opposing ends. The proximal end 54 further comprises a recess 58 in order to receive the distal end of the connection element 36, or, in particular, the latching element 38 in this proximal end 54. In this embodiment, the connection pin 52 is oriented in that way that it runs transversely to the central longitudinal axis 28. Also, the connection pin 52 is arranged parallel to the pivot axis 26.

The elongated opening 48 comprises two opposing longer walls 60 and 62. Herein, the longer wall 60 can be regarded as the distal wall, wherein the longer wall 62 is the proximal wall.

The distal longer wall 60 comprises in this embodiment three projections 64, 64' and 64". The proximal longer wall 62 comprises two projections 66 and 66'. Therefore, these projections 64, 64', 64", 66 and 66' are arranged within the elongated opening.

The roller 50 connects the pivotable jaw part 24 to the latching element 38 in that way that an axial movement of the connection element 36 and, consequently, of the latching element 38, which are a result from an axial movement of the force transmission element 30, results in a movement of the roller 50 within the elongated opening 48. As the roller 50 fits between the longer walls 60 and 62, the movement is only possible along the length of the elongated opening 48. As an axial movement of the latching element 38 results in a movement of the roller 50 that is transverse to the central longitudinal axis 28, and given the rotational arrangement of the pivotable jaw part 24 via the pivot axis 26, the result of such an axial movement of the force transmission element 30 and, hence, the latching element 38, results in a pivot of the pivotable jaw part 24, as it will be described in more detail hereinafter with reference to FIGS. 4a through 4d. These explanations of the medical instrument as described in the following are merely described with the roller 50 by way of example. The same explanations are also valid for devices comprising only the connection pin 52 or a connection pin 164 that runs within the elongated opening 48 and that will be described in more detail later on.

Figure 2:
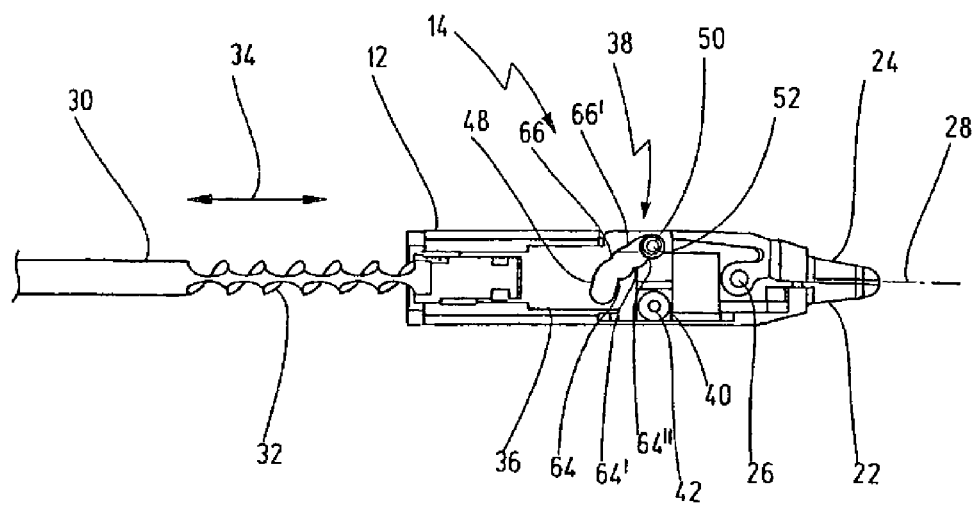
FIG. 2 shows a distal portion of an instrument according to the present invention shown in a sectional view along its longitudinal axis.
Figure 4A:
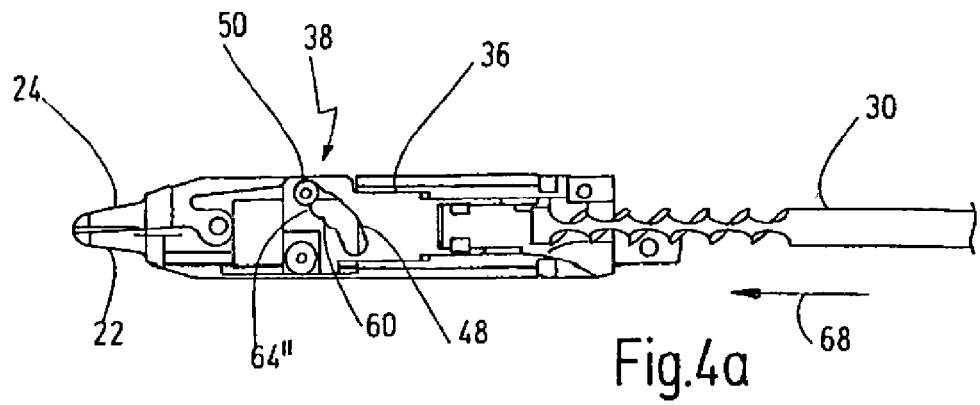

FIG. 4a shows an arrangement wherein the jaw parts 22 and 24 are closed, comparable to the representation of FIG. 2.

In this state, the force transmission element 30 as well as the connection element 36 and, consequently, the latching element 38 are in their furthermost proximal position. In this position, the roller 50 is arranged within the elongated opening 48 between the distal end of this elongated opening 48 and the first projection 64" of the longer wall 60.

Figure 4B:
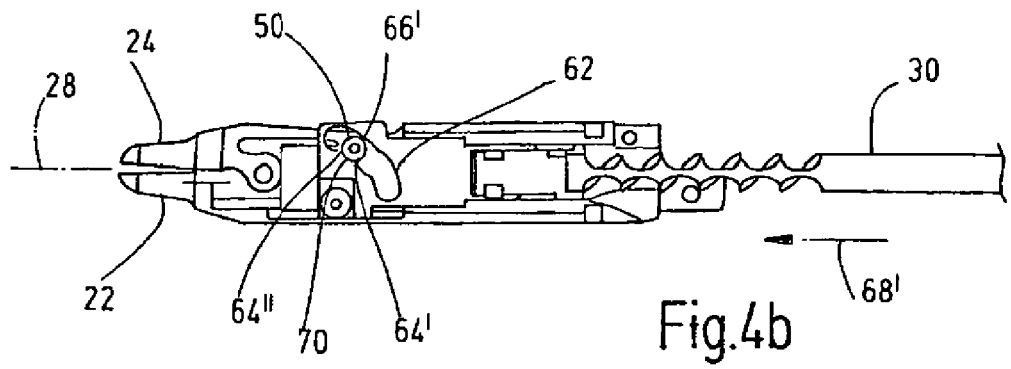

In order to get to the first opening step, as it is shown in FIG. 4b, the latching element 38 has to be moved distally. This is done by a distal movement of the connection element 36 via the force transmission element 30. This movement is implied by arrow 68 of FIG. 4a and can be done by an operator by pushing the operating element 20, for example. By the force applied on the latching element 38, the roller 50 is able to overcome the barrier given by the projection 64". Accordingly, the roller 50 reaches a position as shown in FIG. 4b. In this position, the roller 50 is arranged between the projections 64" and 64'. The roller 50 now lies in a well 70. This well 70 is formed by the projections 64' and 64". In order to avoid a loose arrangement in this well 70, the roller 50 is held in this well additionally by the projection 66' of the longer wall 62. This projection 66' is arranged opposite to the well 70. As the projections 64', 64" and 66' as well as the well 70 are arranged in that way that they perfectly accommodate the roller 50 in this position, the roller 50 is held or latched in this position via form-fit. Such a form-fit occurs as well in the aforementioned most distal position of the roller 50 in the elongated opening 48 as well as in the following latched positions described in the context of FIGS. 4c and 4d.

Since the roller 50 has undergone a movement transverse to that of the central longitudinal axis 28, and since it moved in fact closer to the central longitudinal axis 28 compared to the state of FIG. 4a, the pivotable jaw part 24 pivoted slightly to a small opening of the jaw parts 24 and 22. This is the result of the lever-like arrangement of the pivotable jaw part 24 via pivot axis 26.

Figure 4C:
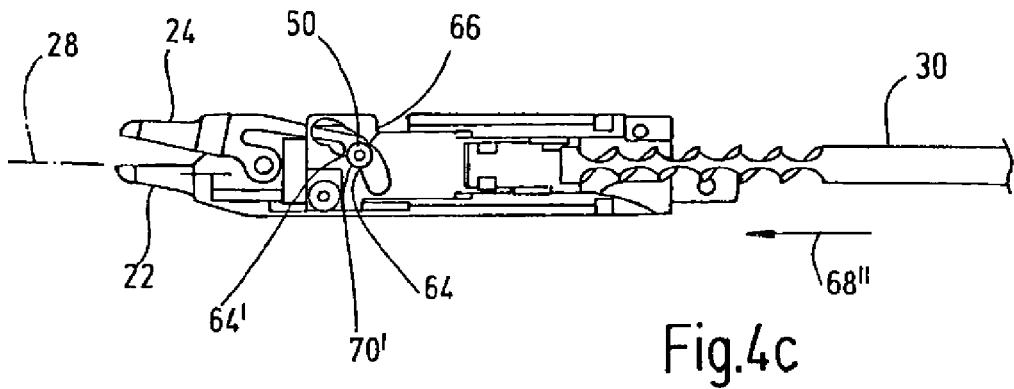

By a further distal movement of the force transmission element 30, as implied by arrow 68', the roller 50 is now able to overcome the barrier given by the projection 64'. Therefore, a further lateral movement of the roller 50 transverse to the central longitudinal axis 28 occurs, as the roller 50 moves further proximal in the elongated opening 48. The result of this further movement is shown in FIG. 4c.

Herein, the roller 50 now is located between projections 64' and 64 in a well 70'. The aforementioned form-fit in this position is realized by the projection 66 of the longer wall 62. This projection 66 is arranged opposite from well 70'. The result is an even more enlarged opening of jaw parts 22 and 24 compared to the representation and state of FIG. 4b.

Figure 4D:
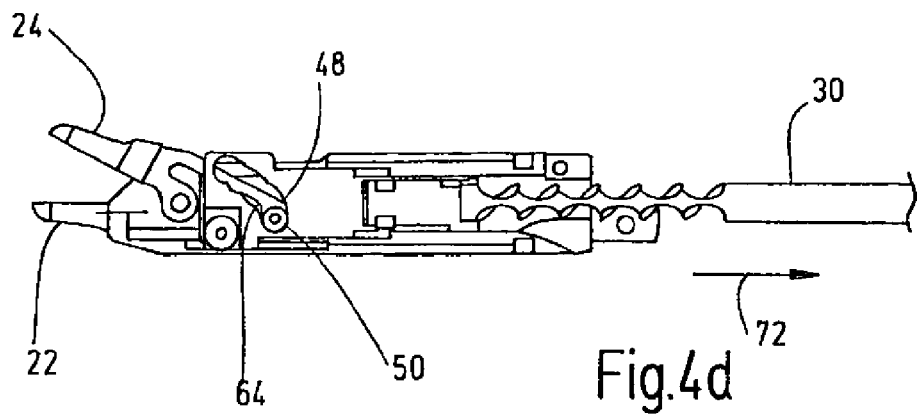

A further movement of the force transmission element 30 in the distal direction, as implied by arrow 68", leads to the state shown in FIG. 4d. Here, the roller 50 overcame the barrier of the projection 64 of longer wall 60. The roller 50 thereby ends in the most proximal position in the elongated opening 48 of the instrument of the embodiment of the present invention shown here. Accordingly, the pivotable jaw part 24 shows in this state in FIG. 4d the largest possible opening for this embodiment.

Each of the shown positions in FIG. 4a through 4d forms a latched position according to the present invention. In this embodiment, the medical instrument comprises four such latching positions. However, by equipping the latching element 38 with more or fewer projections 64 and 66, alternate numbers of latching positions are possible and easy to achieve.

Although the mechanism shown throughout FIGS. 4a to 4d is described in the context of an opening of the jaw parts 22 and 24, i.e. a pivot of the pivotable jaw part 24, the same mechanism works in the opposite direction, meaning for a closing of the jaw parts 22 and 24. Therefore, the force transmission element 30 has to be moved in the proximal direction. This is indicated by arrow 72 in FIG. 4d. This can, for example, be done by an operator by pulling on operating element 20.

The closing procedure works apparently just opposite to the opening procedure, thereby overcoming the aforementioned barriers of the projections 64, 64' and 64" basically in the opposite direction.

Figure 5:
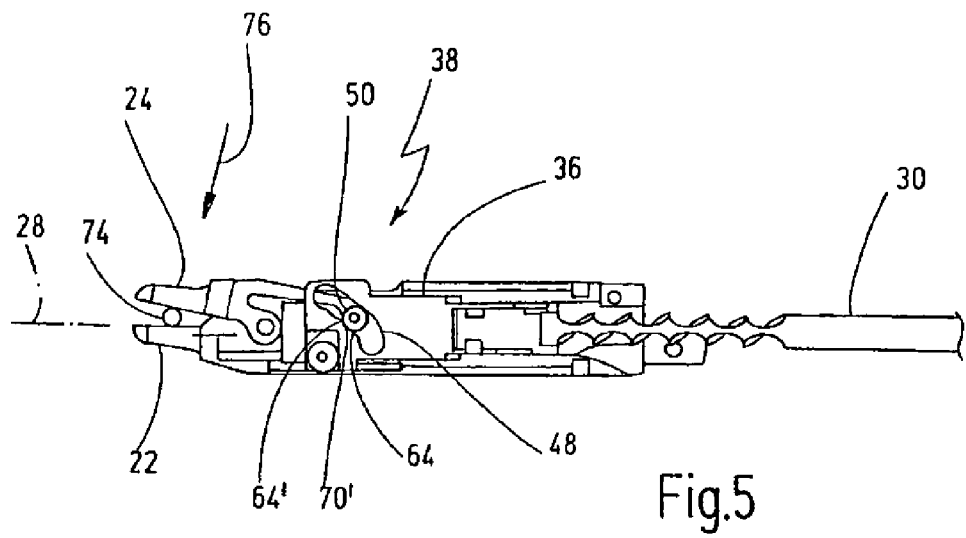
FIG. 5 shows a schematic representation of a distal portion of an instrument according to the present invention grasping a larger object.
Figure 6:
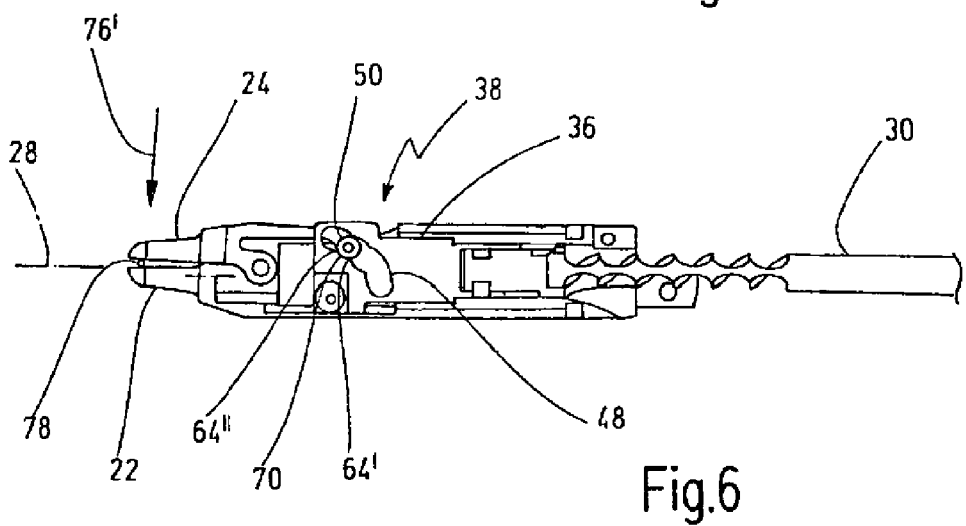
FIG. 6 shows a schematic representation according to FIG. 5, wherein the instrument is grasping a smaller object.

This shall be described in the context of the following FIGS. 5 and 6, wherein it is shown and described how objects are grasped by an instrument of the present invention.

In FIG. 5, a large needle 74 is grasped by the jaw parts 22 and 24. This is achieved by arranging the needle 74 between the jaw parts 22 and 24 and pulling of the force transmission element 30, e.g. via the operating element 20, by an operator. Pulling of the force transmission element 30 results in a proximal movement of the force transmission element 30 and, accordingly, of the connection element 36 comprising the latching element 38. Thereby, with reference to FIG. 4d, the roller 50 is able to overcome the barrier of the projection 64 and, accordingly, moves distal within the elongated opening 48 into well 70', i.e. between projections 64 and 64'. In this position of the pivotable jaw part 24 with respect to the jaw part 22, the needle 74 is held between these jaw parts 22 and 24. The roller 50 is, as already mentioned, in this state latched in the well 70'. Further pulling of the force transmission element 30, i.e. transmission of force in the proximal direction, results in an exertion of force by the well 70' as well as the projection 64' on the roller 50 in a direction away from the central longitudinal axis 28. This results in a transferred force as indicated by arrow 76 because of the pivotable arrangement of the jaw part 24 via the pivot axis 26. In other words, further pulling of the force transmission element 30, or the operating element 20, for example, results in a tight grasp of the object, here the needle 74.

A further movement of the roller 50 in the following well 70 in the distal direction is not possible in this example, as this requires a significant larger pivot of the pivotable jaw part 24 which is hindered by the needle 74.

Showing the case wherein a smaller needle 78 shall be grasped by the jaw parts 22 and 24, FIG. 6 shows that in such an example the roller 50 may move within the elongated opening 48 also over the second projection 64', starting from the opening state of FIG. 4d. This results in a position of the roller 50 within well 70 and in between of the projections 64' and 64".

In this example, with the smaller needle 78, the roller 50 also stays as well in this latched position. This latching position is, in this case, formed by the well 70 and further by the projections 64' and 64".

By further pulling of the force transmission element 30, as already described before in the context of FIG. 5, a force is applied to the roller 50 via the well 70 and projection 64" which is directed in a direction away from the central longitudinal axis 28. This results in a transferred force at the pivotable jaw part 24 indicated by arrow 76', and, accordingly, to a tight grasp of the small needle 78.

Comparing the examples shown in FIG. 5 and FIG. 6, with a large needle 74 and a smaller needle 78, it becomes apparent that the forces applied to the parts of the latching mechanism formed by the latching element 38, are basically of the same amount. Since the necessary closure of the jaw parts 22 and 24 is managed via the latching element 38 comprising the aforementioned latching positions, formed by either the distal or proximal end of the elongated opening 48 or the wells 70 and 70' and the projections 64, 64' and 64", the start point for the exertion of a force in order to tightly grasp an object, here the needles 74 and 78, is the respective latching position. In contrast to this, in EP 1 872 729 A1, mentioned at the outset, there is only one latching position and a flexible latching element 38, responsible also for the grasp of the respective object, which undergoes different strains and bendings, dependent of the object that shall be grasped.

Having the plurality of starting points, i.e. latching positions, and, therefore, almost the same force and strains that act on the parts of the latching element 38, results in a decrease of stress to the parts of the present medical instrument and, accordingly, to a lower risk of damages and cost-intensive repairs.

Further, this grasping force for the objects, here the needles 74 and 78, which stays nearly the same as already mentioned, allows the grasp of the needles to be optimal, independent of the needles' size.

Further, such an arrangement allows a very large jaw opening as shown in FIG. 4d, as the elongated opening 48 can be manufactured in that way that its proximal end runs very deep within the latching element 38 of the connection element 36.

In order to achieve a certain flexibility within this latching mechanism, the proximal portion 54 of the pivotable jaw part 24 is equipped with a certain flexibility in one embodiment of the present invention. Thereby, an accidentally and unwanted stronger force applied to the force transmission element 30 is able to be compensated by this flexible proximal part 54 of the jaw part 24. This avoids the damaging of the parts of the latching mechanism 38.

As mentioned before, medical instruments 100 and 150 shall be described in the following as additional embodiments according to the present invention.

Figure 7:
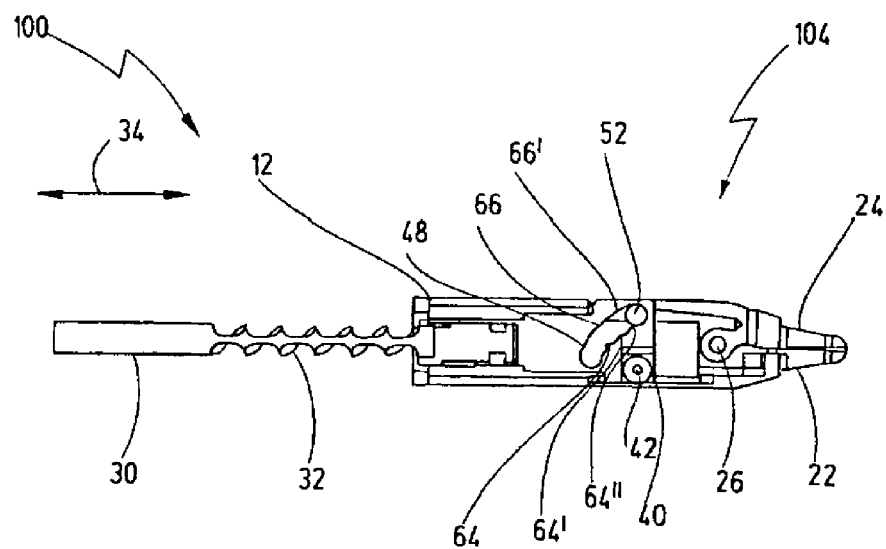
FIG. 7 shows a further embodiment of a distal portion of an instrument according to the present invention shown in a sectional view along its longitudinal axis as in FIG. 2.
Figure 8:
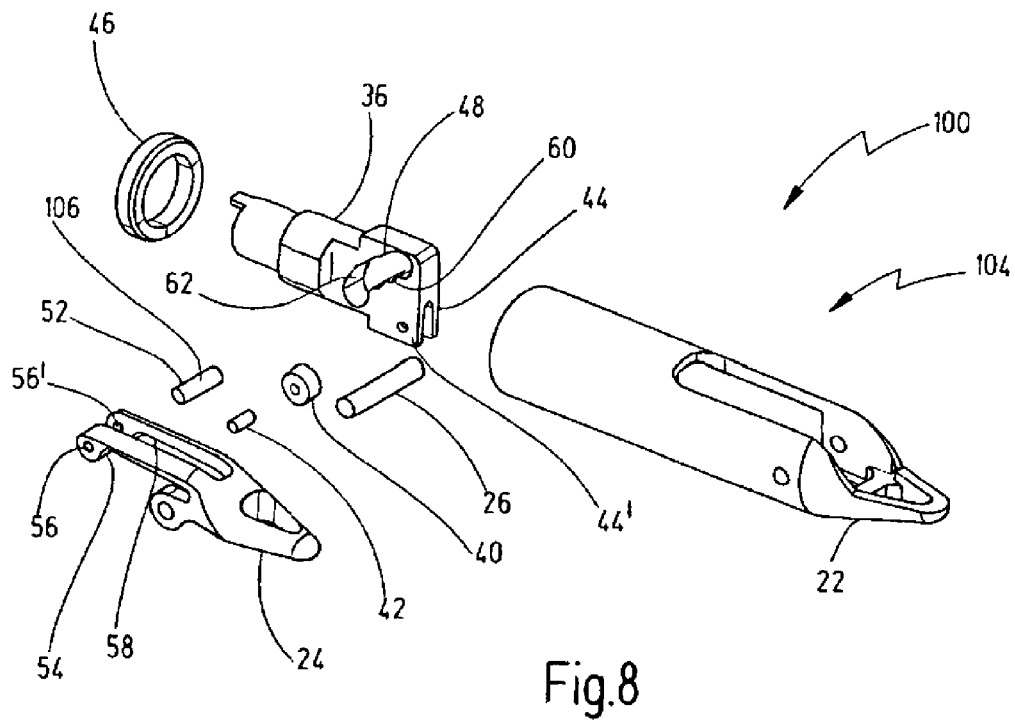
FIG. 8 shows an exploded view of the distal portion shown in FIG. 7 as in FIG. 3.

The medical instrument 100 is almost identical to the medical instrument 10 as described before. In the following description and the drawings, the parts identical to that parts as described in the context of the medical instrument 10 are designated by the same reference signs. The medical instrument 100 will be described in the following by reference to FIGS. 7 and 8 showing a distal end 104 of this medical instrument 100. The parts of the medical instrument 100 not shown in FIGS. 7 and 8 shall be considered as identical to the respective parts in the medical instrument 10.

The difference between medical instrument 100 and medical instrument 10 lies in the connection pin 52. Where in the exemplary embodiment of the medical instrument 10 the connection pin 52 comprises the roller 50 in order to reduce the friction when the connection pin 52 moves through the elongated opening 48 the connection pin 52 is received directly within the elongated opening 48 in the medical instrument 100. As mentioned before the roller 50 present in the description within the context of FIGS. 4a to 6 was merely used by way of example. Accordingly, all the descriptions and explanations made within the context of FIGS. 4a to 6 demonstrating the functioning of the medical instruments according to the present invention can be used in the same way to describe the functioning of the medical instrument 100 or the medical instrument 150, which will be described later, just by replacing the wording "roller 50" in the explanations mentioned above by "connection pin 52" or "connection pin 164", respectively.

Accordingly, the connection pin 52 is accommodated within the elongated opening 48 and interacts in the described way with the projections 64, 64', 64", 66 and 66'. Therefore, the connection pin 52 of this embodiment is designed to be received in an optimal way for the desired sliding function.

The usage of just the connection pin 52 allows for an easy cleaning of the whole device. Further, it simplifies the construction.

In order to avoid unwanted interferences in the opening or closing procedures of the pivotable jaw part 24 by interactions of the connection pin 52 within the elongated opening 48, i.e. on the opposing walls 60 or 62 by friction, the connection pin 52 may comprise a surface having a reduced coefficient of friction with the material of the opposing walls 60 or 62. Such a surface may result from a low friction coating 106. This low friction coating 106 may cover the whole connection pin 52 as shown here or may just be applied to the areas necessary in order to reduce the friction between the connection pin 52 and the elongated opening 48 with its walls 60 and 62.

An example for a coating that may also act as a low friction coating 106 is Polytetrafluoroethylene (PTFE). PTFE has the advantage that it provides a surface with a reduced coefficient of friction as mentioned before and is also able to be submitted to the generally used sterilizing methods involving autoclaves and chemicals. Further, the in general smooth surface of PTFE makes it harder for dirt and bacteria to get stuck on such a surface and makes it easier to clean.

Although the description of the connection pin 52 is made in this context with a low friction coating 106 it goes without mentioning that it is also possible to provide the same medical instruments without such a coating on the connection pin 52. Further, providing a connection pin 52 that is made of a material providing a reduced coefficient of friction like PTFE lies also within the scope of the present invention.

Figure 9:
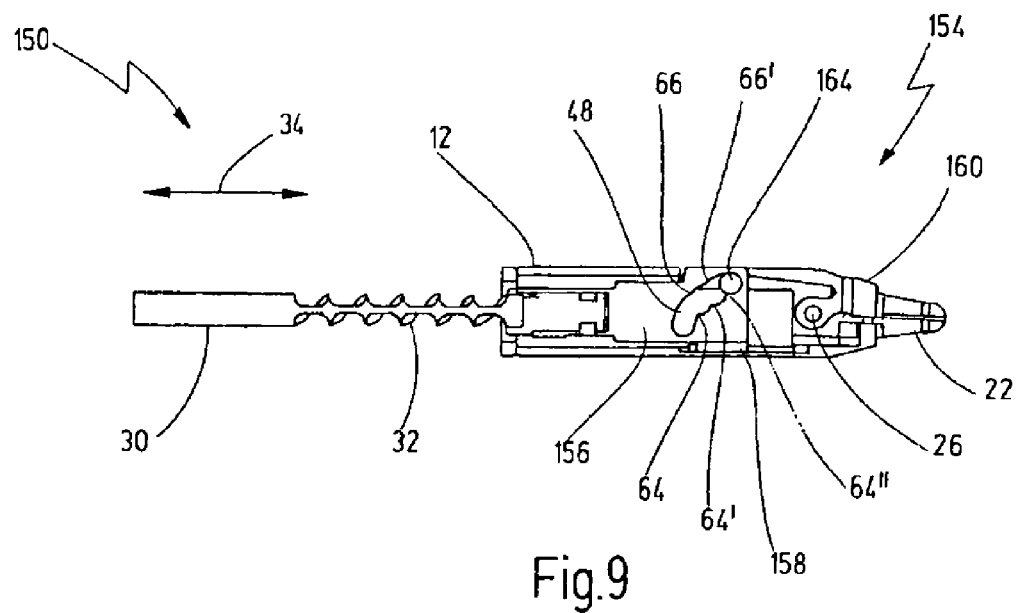
FIG. 9 shows another embodiment of an instrument according to the present invention similar to FIG. 7 without a sliding roller.
Figure 10:
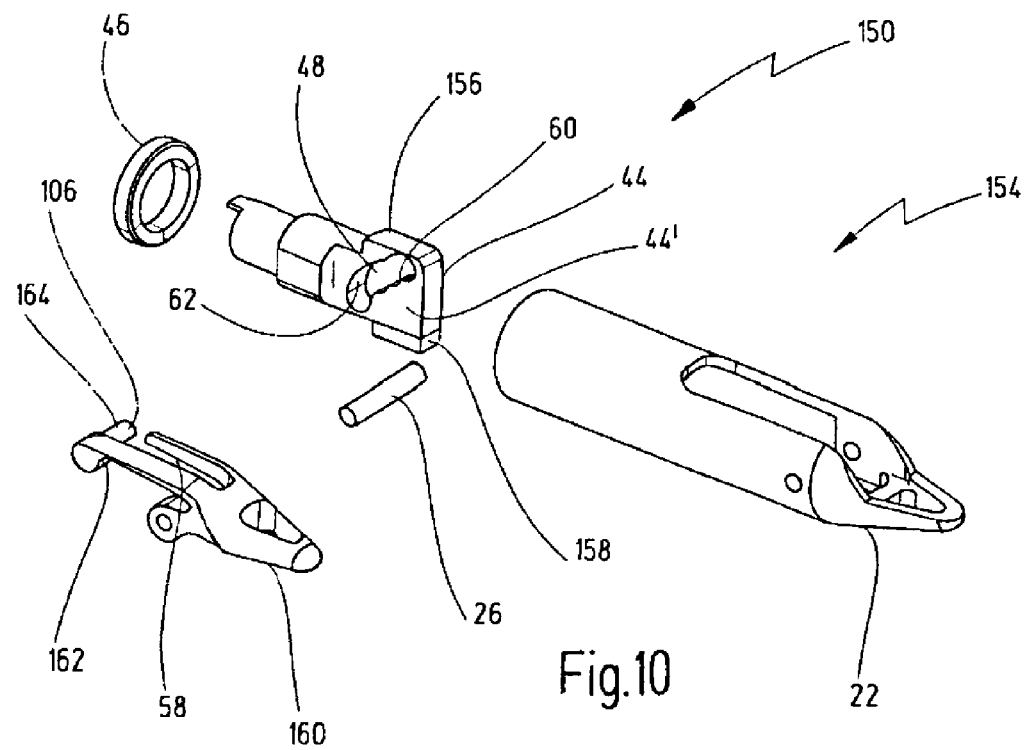
FIG. 10 shows an exploded view of the distal portion shown in FIG. 9.

The medical instrument 150 will now be described by reference to FIGS. 9 and 10. As the medical instrument 100 this medical instrument 150 is in most parts identical to the medical instrument 10 and only differs in a distal end 154 and the design of the pivotable jaw part 160 which will be described in the following. The parts not shown in FIGS. 9 and 10 shall be considered as identical to the medical instrument 10. Further, identical parts with respect to the medical instrument 10 and 100 will be described and designated by the same reference signs.

The medical instrument 150 comprises the same latching mechanism as the medical instrument 100. This means that a connection pin 164 is arranged moveably directly within the elongated opening 48. Hence, no roller 50 is used in the embodiment of the medical instrument 150. Accordingly, all the explanations with respect to connection pin 52 made within the context of FIGS. 7 and 8 describing the function of the latching mechanism are also valid for the medical instrument 150. However, the medical instrument 150 differs from the aforementioned medical instruments 10 and 100 in the pivotable jaw part 160. Instead of comprising two openings 56 and 56' at its proximal end 162 the jaw part 160 comprises a connection pin 164 directly attached to it. This connection pin 164 can be designed as the connection pin 52. This means, that the connection pin 164 may as well comprise a low friction coating 106.

A further difference of the medical instrument 150 to the medical instrument 10 is that the medical instrument 150 does not comprise the sliding roller 40 arranged at a connection element 156.

Aside from using the sliding roller 40 as mentioned before it is also possible to use a connection element 156 that may slide within the shaft 12 of the medical instrument 150 directly.

In order to provide a reduced friction of the connection element 156 of the medical instrument 150, the connection element 156 comprises a low friction coating 158. Thereby, the coefficient of friction with the inner wall of the shaft 12 is reduced. This provides an alternative to the sliding roller 40 of the medical instruments 10 or 100.

As described before within the context of the connection pin 52 in FIGS. 7 and 8, the low friction coating may be realized by a Polytetrafluoroethylene coating. This kind of coating has the same advantages as mentioned before, i.e. that the friction is reduced as desired and that cleaning and sterilizing are possible under the conditions regularly used for medical instruments.

Apart from using just a low friction coating 158, it is also possible that a small element of a low friction material is attached to the connection element 156 replacing the part of the connection element 156 which comprises the low friction coating 158. Further, the whole connection element 156 may be made out of such a low friction material. In all the mentioned cases, the connection element 156 comprises a surface having a reduced coefficient of friction. The aforementioned low friction materials can also be Polytetrafluoroethylene.

What is claimed is:

1. A medical instrument for grasping an object, in particular a surgical needle holder, comprising:
    an elongated shaft, having a proximal and a distal end,
    an axially movable force transmission element running within said shaft,
    two jaw parts arranged at said distal end of said shaft, at least one of said jaw parts being pivotable with respect to the other one of said jaw parts, a connection element for operatively connecting said force transmission element with said at least one pivotable jaw part,
a connection pin,
a handle arranged at said proximal end of said shaft, said handle having at least one operating element for moving said at least one pivotable jaw part, and
a latching mechanism,
said latching mechanism comprising:
at least one latching element being at least a part of said connection element, and
at least three latching positions,
said latching element comprising an elongated opening to accommodate said connection pin,
said elongated opening comprising:
two opposing longer walls, and
periodical projections on at least one of said opposing walls along the length of said elongated opening,
wherein said at least one pivotable jaw part is pivotable between a grasp state for grasping said object between said jaw parts and a release state for releasing said object by said operating element, and said axially movable force transmission element is operatively connected with said at least one operating element and with said at least one pivotable jaw part via said connection element,
said at least one pivotable jaw part can be immobilized in said grasp state by said latching mechanism,
wherein said latching element is operatively connected to said force transmission element and said at least one pivotable jaw part,
said at least one pivotable jaw part being connected with said latching element via said connection pin, and
wherein said elongated opening is divided in several sections along its length, said sections being formed by said periodical projections, and wherein each of said sections forms one of said latching positions, such that said at least one pivotable jaw part pivots stepwise from one stable latched position to another stable latched position, when said transmission element is moved axially.

2. The instrument of claim 1, wherein said latching mechanism comprises three to eight latching positions.

3. The instrument of claim 1, wherein said latching mechanism comprises three to five latching positions.

4. The instrument of claim 1, wherein one of said latching positions forms said grasp state.

5. The instrument of claim 4, wherein said latched position forming said grasp state and a latched position forming said release state are achieved by the furthermost movement of said force transmission element in one respective axial direction when interacting with said object to grasp.

6. The instrument of claim 1, wherein said force transmission element comprises a distal end, and wherein said connection element is arranged at said distal end of said force transmission element in that way that it undergoes the same axial movements as said force transmission element.

7. The instrument of claim 1, wherein said elongated opening is arranged in that way, that a movement of said latching element by an axial movement of said force transmission element results in a pivot of said at least one pivotable jaw part by movement of said connection pin within said elongated opening.

8. The instrument of claim 1, wherein said elongated opening is arc shaped.

9. The instrument of claim 1, wherein said latching element comprises two opposing faces and said elongated opening passes through said latching element from one of said faces to the other one of said faces.

10. The instrument of claim 9, wherein said connection pin passes substantially through said elongated opening.

11. The instrument of claim 1, wherein said connection pin can move from one of said sections to another one of said sections being latched in each.

12. The instrument of claim 1, wherein said connection pin comprises a surface having a reduced coefficient of friction.

13. The instrument of claim 1, wherein said connection pin comprises a surface of Polytetrafluoroethylene.

14. The instrument of claim 1, wherein in said at least three latching positions, said connection pin lies in a well between two of said periodical projections.

15. The instrument of claim 1, wherein said at least one pivotable jaw part comprises a proximal portion being elastically deformable.

16. The instrument of claim 1, wherein said connection pin comprises a roller, said roller being arranged between said opposing walls and being moveable along the length of said elongated opening.

17. The instrument of claim 16, wherein each of said sections accommodates said roller via form-fit, and wherein said roller is able to move from one of said sections to another one of said sections.

18. The instrument of claim 1, wherein said connection element comprises at least one sliding roller, and wherein said connection element is arranged in said shaft and gets in contact with said shaft via said sliding roller.

19. A medical instrument for grasping an object, in particular a surgical needle holder, comprising:
an elongated shaft, having a proximal and a distal end,
an axially movable force transmission element running within said shaft,
two jaw parts arranged at said distal end of said shaft, at least one of said jaw parts being pivotable with respect to the other one of said jaw parts,
a connection element for operatively connecting said force transmission element with said at least one pivotable jaw part,
a connection pin,
a handle arranged at said proximal end of said shaft,
said handle having at least one operating element for moving said at least one pivotable jaw part,
a latching mechanism,
said latching mechanism comprising:
at least one latching element being at least a part of said connection element, and
at least three latching positions,
said latching element comprising:
two opposing faces, and
an elongated opening to accommodate said connection pin, comprising two opposing longer walls, said elongated opening passing through said latching element from one of said faces to the other one of said faces,
wherein said at least one pivotable jaw part is pivotable between a grasp state for grasping said object between said jaw parts and a release state for releasing said object, and said axially movable force transmission element is operatively connected with said at least one operating element and with said at least one pivotable jaw part via said connection element, said at least one pivotable jaw part can be immobilized in said grasp state by said latching mechanism,
wherein said latching element is operatively connected to said transmission element and said at least one pivotable jaw part,
said at least one pivotable jaw part being connected with said latching element via said connection pin, wherein said connection pin passes substantially through said elongated opening, and said elongated opening is divided in several sections along its length, and wherein each of said sections forms one of said latching positions, such that said at least one pivotable jaw part pivots stepwise from one stable latched position to another stable latched position, when said transmission element is moved axially, and wherein said elongated opening comprises periodical projections on at least one of said opposing walls along the length of said elongated opening.

20. The instrument of claim 19, wherein said latching mechanism comprises three to eight latching positions.

21. The instrument of claim 19, wherein said latching mechanism comprises three to five latching positions.

22. The instrument of claim 19, wherein one of said latching positions forms said grasp state.

23. The instrument of claim 22, wherein said latched position forming said grasp state and a latched position forming said release state are achieved by the furthermost movement of said force transmission element in one respective axial direction when interacting with said object to grasp.

24. The instrument of claim 19, wherein said force transmission element comprises a distal end, and wherein said connection element is arranged at said distal end of said force transmission element in that way that it undergoes the same axial movements as said force transmission element.

25. The instrument of claim 19, wherein said elongated opening is arranged in that way, that a movement of said latching element by an axial movement of said force transmission element results in a pivot of said at least one pivotable jaw part by movement of said connection pin within said elongated opening.

26. The instrument of claim 19, wherein said elongated opening is arc shaped.

27. The instrument of claim 18, wherein said connection pin can move from one of said sections to another one of said sections being latched in each.

28. The instrument of claim 19, wherein said connection pin comprises a surface having a reduced coefficient of friction.

29. The instrument of claim 19, wherein said connection pin comprises a surface of Polytetrafluoroethylene.

30. The instrument of claim 19, wherein said at least one pivotable jaw part comprises a proximal portion being elastically deformable.

31. The instrument of claim 19, wherein in said at least three latching positions, said connection pin lies in a well between two of said periodical projections.

32. The instrument of claim 19, wherein said connection pin comprises a roller, said roller being arranged between said opposing walls and being moveable along the length of said elongated opening.

33. The instrument of claim 32, wherein each of said sections accommodates said roller via form-fit, and wherein said roller is able to move from one of said sections to another one of said sections.

34. The instrument of claim 19, wherein said connection element comprises at least one sliding roller, and wherein said connection element is arranged in said shaft and gets in contact with said shaft via said sliding roller.

* * * * *